(12) United States Patent
Hagemeyer et al.

(10) Patent No.: US 8,466,082 B2
(45) Date of Patent: *Jun. 18, 2013

(54) PD/AU SHELL CATALYST CONTAINING HFO$_2$, PROCESSES FOR THE PREPARATION AND USE THEREOF

(75) Inventors: Alfred Hagemeyer, Bad Aibling (DE); Gerhard Mestl, Munich (DE); Peter Scheck, Gilching (DE)

(73) Assignee: Sued-Chemie IP GmbH & Co. KG, Munich (DE)

( * ) Notice: Subject to any disclaimer, the term of this patent is extended or adjusted under 35 U.S.C. 154(b) by 341 days.

This patent is subject to a terminal disclaimer.

(21) Appl. No.: 12/601,399

(22) PCT Filed: May 30, 2008

(86) PCT No.: PCT/EP2008/004333
§ 371 (c)(1),
(2), (4) Date: Jun. 9, 2010

(87) PCT Pub. No.: WO2008/145392
PCT Pub. Date: Dec. 4, 2008

(65) Prior Publication Data
US 2011/0166010 A1    Jul. 7, 2011

(30) Foreign Application Priority Data
May 31, 2007   (DE) .................. 10 2007 025 443

(51) Int. Cl.
| | | |
|---|---|---|
| *B01J 20/00* | (2006.01) | |
| *B01J 21/00* | (2006.01) | |
| *B01J 21/04* | (2006.01) | |
| *B01J 23/00* | (2006.01) | |
| *B01J 23/02* | (2006.01) | |
| *B01J 23/04* | (2006.01) | |
| *B01J 23/08* | (2006.01) | |
| *B01J 23/40* | (2006.01) | |
| *B01J 23/42* | (2006.01) | |
| *B01J 23/44* | (2006.01) | |
| *B01J 23/56* | (2006.01) | |
| *B01J 23/58* | (2006.01) | |

(52) U.S. Cl.
USPC .......... 502/242; 502/243; 502/262; 502/263; 502/327; 502/330; 502/332; 502/333; 502/339; 502/344; 502/349; 502/350; 502/351; 502/355; 502/415; 502/439

(58) Field of Classification Search
USPC ............ 502/242, 243, 262, 263, 327, 330, 502/332, 333, 339, 344, 349–351, 355, 415, 502/439
See application file for complete search history.

(56) References Cited

U.S. PATENT DOCUMENTS

| | | | |
|---|---|---|---|
| 2,656,323 A | 10/1953 | Bielawski et al. | |
| 3,252,757 A | 5/1966 | Granquist | |
| 3,259,589 A | 7/1966 | Michalko | |
| 3,565,919 A | 2/1971 | Friedrichsen et al. | |
| 3,617,489 A | 11/1971 | Csicsery | |
| 4,155,730 A | 5/1979 | Biberbach et al. | |
| 4,407,733 A | 10/1983 | Birkenstock et al. | |
| 4,409,410 A | 10/1983 | Cosyns et al. | |
| 4,521,618 A | 6/1985 | Arntz et al. | |
| 4,621,072 A | 11/1986 | Arntz et al. | |
| 4,844,790 A | 7/1989 | Occelli | |
| 4,970,804 A | 11/1990 | Hüttlin | |
| 4,977,126 A | 12/1990 | Mauldin et al. | |
| 4,990,266 A | 2/1991 | Vorlop et al. | |
| 5,015,453 A * | 5/1991 | Chapman ................ | 423/718 |
| 5,066,365 A | 11/1991 | Roscher et al. | |
| 5,145,650 A | 9/1992 | Hüttlin | |
| 5,175,136 A * | 12/1992 | Felthouse ................ | 502/242 |
| 5,179,056 A | 1/1993 | Bartley | |
| 5,189,123 A | 2/1993 | Gropper et al. | |
| 5,213,771 A | 5/1993 | Hilliard et al. | |
| 5,250,487 A | 10/1993 | Wirtz et al. | |
| 5,304,525 A | 4/1994 | Immel et al. | |
| 5,422,329 A | 6/1995 | Wirtz et al. | |
| 5,559,071 A | 9/1996 | Abel et al. | |
| 5,567,839 A | 10/1996 | Gulliver et al. | |
| 5,571,771 A | 11/1996 | Abel et al. | |
| 5,591,688 A * | 1/1997 | Blum et al. ............... | 502/330 |

(Continued)

FOREIGN PATENT DOCUMENTS

| | | |
|---|---|---|
| CA | 2 338 961 | 2/2000 |
| DE | 1 286 021 B1 | 1/1969 |

(Continued)

OTHER PUBLICATIONS

L.A. Boot et al., Characterization of Pre-shaped Zirconia Bodies for Catalytic Applications, Journal of Material Science, vol. 31, 1996, pp. 3115-3121.

(Continued)

*Primary Examiner* — Cam N. Nguyen

(74) *Attorney, Agent, or Firm* — RatnerPrestia

(57) ABSTRACT

A shell catalyst for the preparation of vinyl acetate monomer, comprising an oxidic porous catalyst support with an outer shell, containing metallic Pd and Au, wherein the framework structure of the porous catalyst support contains hafnium oxide units. This shell catalyst is suitable for the preparation of VAM and is characterized by a relatively high activity and VAM selectivity and maintains this activity and selectivity over relatively long service lives. Also, processes for the preparation and use of the shell catalyst.

37 Claims, No Drawings

U.S. PATENT DOCUMENTS

| | | | |
|---|---|---|---|
| 5,622,908 A | 4/1997 | Abel et al. | |
| 5,648,576 A | 7/1997 | Nguyen Than et al. | |
| 5,650,371 A | 7/1997 | Culross | |
| 5,665,667 A | 9/1997 | Lemanski et al. | |
| 5,668,074 A | 9/1997 | Wu et al. | |
| 5,700,753 A | 12/1997 | Wang et al. | |
| 5,753,583 A | 5/1998 | Heineke et al. | |
| 5,801,285 A | 9/1998 | Waldmann et al. | |
| 5,808,136 A | 9/1998 | Tacke et al. | |
| 5,888,472 A * | 3/1999 | Bem et al. | 423/713 |
| 5,935,889 A | 8/1999 | Murrell et al. | |
| 5,990,344 A | 11/1999 | Couves et al. | |
| 6,015,769 A | 1/2000 | Wang | |
| 6,017,847 A | 1/2000 | Wang | |
| 6,074,979 A * | 6/2000 | Hagemeyer et al. | 502/159 |
| 6,090,746 A | 7/2000 | Bönnemann et al. | |
| 6,156,927 A * | 12/2000 | Halcom et al. | 560/245 |
| 6,207,610 B1 * | 3/2001 | Krause et al. | 502/232 |
| 6,228,800 B1 | 5/2001 | Yamaguchi et al. | |
| 6,268,522 B1 | 7/2001 | Hagemeyer et al. | |
| 6,288,295 B1 | 9/2001 | Didillon et al. | |
| 6,313,063 B1 | 11/2001 | Rytter et al. | |
| 6,316,383 B1 * | 11/2001 | Tacke et al. | 502/232 |
| 6,350,717 B1 | 2/2002 | Frenzel et al. | |
| 6,350,900 B1 | 2/2002 | Wang et al. | |
| 6,358,882 B1 * | 3/2002 | Salem et al. | 502/305 |
| 6,367,165 B1 | 4/2002 | Hüttlin | |
| 6,395,676 B2 * | 5/2002 | Blum et al. | 502/330 |
| 6,399,813 B1 * | 6/2002 | Blum et al. | 560/245 |
| 6,420,308 B1 | 7/2002 | Khanmamedova | |
| 6,486,093 B2 | 11/2002 | Wang et al. | |
| 6,492,299 B1 | 12/2002 | Couves et al. | |
| 6,528,453 B2 * | 3/2003 | Baker et al. | 502/325 |
| 6,528,683 B1 | 3/2003 | Heidemann et al. | |
| 6,534,438 B1 * | 3/2003 | Baker et al. | 502/325 |
| 6,534,672 B2 * | 3/2003 | Salem et al. | 560/241 |
| 6,593,270 B1 * | 7/2003 | Krause et al. | 502/328 |
| 6,603,038 B1 | 8/2003 | Hagemeyer et al. | |
| 6,605,739 B1 | 8/2003 | Karim et al. | |
| 6,734,131 B2 | 5/2004 | Shih et al. | |
| 6,797,669 B2 | 9/2004 | Zhang et al. | |
| 6,806,382 B2 * | 10/2004 | Baker et al. | 560/245 |
| 6,821,922 B1 * | 11/2004 | Tacke et al. | 502/330 |
| 6,849,243 B1 | 2/2005 | Hagemeyer et al. | |
| 6,898,869 B2 | 5/2005 | Hüttlin | |
| 6,949,141 B2 | 9/2005 | Hüttlin | |
| 6,987,200 B2 | 1/2006 | Hagemeyer et al. | |
| 6,992,040 B2 | 1/2006 | Müller et al. | |
| 7,288,686 B2 | 10/2007 | Ryu | |
| 7,468,455 B2 * | 12/2008 | Mazanec et al. | 560/243 |
| 7,569,508 B2 | 8/2009 | Zhou et al. | |
| 7,797,854 B2 | 9/2010 | Huettlin | |
| 8,207,327 B2 | 6/2012 | Laar et al. | |
| 2001/0018401 A1 * | 8/2001 | Blum et al. | 502/330 |
| 2001/0048970 A1 * | 12/2001 | Hagemeyer et al. | 427/217 |
| 2002/0028966 A1 * | 3/2002 | Blum et al. | 560/261 |
| 2002/0052290 A1 | 5/2002 | Bowman et al. | |
| 2002/0062039 A1 * | 5/2002 | Salem et al. | 560/261 |
| 2003/0036476 A1 | 2/2003 | Arnold et al. | |
| 2003/0144544 A1 * | 7/2003 | Baker et al. | 560/243 |
| 2003/0187293 A1 | 10/2003 | Birke et al. | |
| 2003/0187294 A1 | 10/2003 | Hagemeyer et al. | |
| 2003/0195114 A1 * | 10/2003 | Tacke et al. | 502/328 |
| 2003/0233012 A1 | 12/2003 | Jackson et al. | |
| 2004/0048937 A1 | 3/2004 | Srinivasan et al. | |
| 2004/0235650 A1 | 11/2004 | Saleh et al. | |
| 2005/0034322 A1 | 2/2005 | Hüttlin | |
| 2005/0181940 A1 | 8/2005 | Wang et al. | |
| 2005/0203320 A1 | 9/2005 | Ryu | |
| 2006/0135809 A1 | 6/2006 | Kimmich et al. | |
| 2006/0266673 A1 | 11/2006 | Rende et al. | |
| 2007/0135302 A1 | 6/2007 | Neto et al. | |
| 2007/0191651 A1 | 8/2007 | Coupard et al. | |
| 2007/0234586 A1 | 10/2007 | Huettlin | |
| 2008/0287290 A1 | 11/2008 | Wang et al. | |
| 2010/0140181 A1 | 6/2010 | Tastayre | |
| 2011/0166010 A1 | 7/2011 | Hagemeyer et al. | |

FOREIGN PATENT DOCUMENTS

| | | |
|---|---|---|
| DE | 27 03 801 A1 | 8/1978 |
| DE | 28 48 978 A1 | 5/1980 |
| DE | 29 45 913 A1 | 6/1981 |
| DE | 31 19 850 A1 | 2/1982 |
| DE | 40 06 935 A1 | 9/1991 |
| DE | 40 39 026 A1 | 6/1992 |
| DE | 44 05 876 A1 | 10/1995 |
| DE | 44 43 705 A1 | 6/1996 |
| DE | 195 34 493 A1 | 3/1997 |
| DE | 195 38 799 A1 | 4/1997 |
| DE | 196 01 861 A1 | 7/1997 |
| DE | 197 34 974 A1 | 2/1999 |
| DE | 197 34 975 A1 | 3/1999 |
| DE | 198 34 569 | 2/2000 |
| DE | 199 04 147 A1 | 8/2000 |
| DE | 199 14 066 A1 | 10/2000 |
| DE | 100 64 084 A1 | 7/2002 |
| DE | 697 11 320 T2 | 7/2002 |
| DE | 102 48 116 B3 | 4/2004 |
| DE | 602 06 752 T2 | 7/2006 |
| DE | 20 2005 003 791 U1 | 8/2006 |
| DE | 10 2005 029 200 A1 | 12/2006 |
| EP | 0 064 301 A1 | 11/1982 |
| EP | 0 370 167 A1 | 5/1990 |
| EP | 0 436 787 A2 | 7/1991 |
| EP | 0 565 952 A1 | 10/1993 |
| EP | 0 634 208 A1 | 1/1995 |
| EP | 0 634 209 A1 | 1/1995 |
| EP | 0 634 214 A1 | 1/1995 |
| EP | 0 723 810 | 7/1996 |
| EP | 0 839 793 A1 | 5/1998 |
| EP | 0 839 797 | 5/1998 |
| EP | 0 882 507 A1 | 12/1998 |
| EP | 0 899 013 A1 | 3/1999 |
| EP | 1 102 635 B1 | 5/2001 |
| EP | 1 323 469 A2 | 7/2003 |
| EP | 1 452 230 A1 | 9/2004 |
| EP | 1 979 073 | 7/2007 |
| GB | 1 258 371 | 1/1970 |
| GB | 1 229 749 | 4/1971 |
| GB | 1 283 737 | 8/1972 |
| JP | 2003-527962 | 9/2003 |
| JP | 2006-239588 | 9/2006 |
| JP | 2006-255600 | 9/2006 |
| WO | WO 98/14274 | 4/1998 |
| WO | WO 98/18553 A1 | 5/1998 |
| WO | WO 98/37102 | 8/1998 |
| WO | WO 99/22860 | 5/1999 |
| WO | WO 99/62632 | 12/1999 |
| WO | WO 00/58008 A1 | 10/2000 |
| WO | WO 02/100527 A1 | 12/2002 |
| WO | WO 2005/061107 | 7/2005 |
| WO | WO 2005/065821 | 7/2005 |
| WO | WO 2006/027009 A1 | 3/2006 |
| WO | WO 2006/045606 A1 | 5/2006 |
| WO | WO 2008/107050 A1 | 9/2008 |

OTHER PUBLICATIONS

International Search Report PCT/EP2008/004333 dated Nov. 13, 2008.
Kohl et al., Gas purification, 5$^{th}$ Edition, Gulf Publishing Company pp. 40-73 (1997).
Komai et al., Journal of Catalysis 120, 370-376 (1989).
Lehrbuch de anorganischen Chemie, Hollemann Wiberg, de Gruyter 102, Auflage, (ISBN 978-3-11-017770-1), pp. 955-970, term Schichtsllkate (2007).
Römpp Chemical Dictionary, 10$^{th}$ Edition (1997), Georg Thieme Verlag, at pp. 374-375.
Römpp Chemical Dictionary, 10$^{th}$ Edition (1997), Georg Thieme Verlag, at pp. 3427-3428.
Reddy et al., Fluor's Econamine FG Plus$^{SM}$ Technology, presented at the Second National Conference on Carbon Sequestration, National Energy Technology Department of Energy, Alexandria, VA, USE, pp. 1-11, May 5-8, 2003.

Textbook of Inorganic Chemistry, Hollemann Wiberg, de Gruyter, 102$^{nd}$ Edition, 2007 (ISBN 978-3-11-017770-1), at pp. 955-959, 965-970.
Usubharatana et al., Energy Procedia, vol. 1, Issue 1, pp. 95-102 (2009).
Office Action in U.S. Appl. No. 12/601,419 dated Jan. 30, 2012.
Response filed in U.S. Appl. No. 12/601,419 on May 30, 2012.
Office Action in U.S. Appl. No. 12/601,419 dated Aug. 6, 2012.
Response filed in U.S. Appl. No. 12/601,419 dated Oct. 5, 2012.
Office Action in U.S. Appl. No. 12/601,420 dated Jun. 18, 2012.
Response filed in U.S. Appl. No. 12/601,420 on Oct. 18, 2012.
Office Action in U.S. Appl. No. 12/601,777 dated Jan. 9, 2012.
Response filed in U.S. Appl. No. 12/601,777 on May 9, 2012.
Office Action in U.S. Appl. No. 12/601,777 dated Jun. 12, 2012.
Response filed in U.S. Appl. No. 12/601,777 on Sep. 12, 2012.
Office Action in U.S. Appl. No. 12/602,315 dated Aug. 16, 2012.
Office Action in U.S. Appl. No. 12/601,900 dated Jan. 4, 2012.
Elliott P. Barrett et al., "The Determination of Pore Volume and Area Distributions in Porous Substances. I. Computations from Nitrogen Isotherms," *J. Am. Chem. Soc.*, vol. 73, 1951, pp. 373-380.
Stephen Brunauer et al., "Adsorption of Gases in Multimolecular Layers," *J. Am. Chem. Soc.*, vol. 60, 1938, pp. 309-319.
Office Action in U.S. Appl. No. 12/601,985 dated Feb. 7, 2013.

* cited by examiner

PD/AU SHELL CATALYST CONTAINING HFO₂, PROCESSES FOR THE PREPARATION AND USE THEREOF

CROSS-REFERENCE TO RELATED APPLICATION

This is a National Phase application of PCT application number PCT/EP2008/004333, filed May 30, 2008, which claims priority benefit of German application number DE 10 2007 025 443.3, filed May 31, 2007, the content of such applications being incorporated herein by reference.

FIELD OF THE INVENTION

The present invention relates to a shell catalyst for the preparation of vinyl acetate monomer (VAM), comprising an oxidic porous catalyst support which contains hafnium oxide units, said support having an outer shell which contains metallic Pd and Au, and also the preparation thereof.

BACKGROUND OF THE INVENTION

VAM is an important monomer building block in the preparation of plastic polymers. The main fields of use of VAM are i.a. the preparation of polyvinyl acetate, polyvinyl alcohol and polyvinyl acetal and also co- and terpolymerization with other monomers such as for example ethylene, vinyl chloride, acrylate, maleinate, fumarate and vinyl laurate.

DESCRIPTION OF THE INVENTION

VAM is prepared predominantly in the gas phase from acetic acid and ethylene by reaction with oxygen, wherein the catalysts used for this synthesis preferably contain Pd and Au as catalytically active metals and also an alkali metal component as promoter, preferably potassium in the form of its acetate. The catalytically active metals Pd and Au are presumably not in the form of metal particles of the respective pure metal, but rather in the form of Pd/Au alloy particles of possibly different composition, although non-alloyed particles cannot be ruled out.

Currently, VAM is predominantly prepared by means of so-called shell catalysts in which the catalytically active metals of the catalyst having a catalyst support formed as a shaped body are not completely present in the entire shaped body, but rather are contained only in an outer area of greater or lesser width, the so-called shell of the catalyst support shaped body (cf. on this EP 565 952 A1, EP 634 214 A1, EP 634 209 A1 and EP 634 208 A1). The areas of the support lying further inside are almost free of the catalytically active metals. With the help of shell catalysts, a more selective reaction control is possible in many cases than with catalysts in which the supports are impregnated into the core of the support with the catalytically active components ("impregnated through").

The shell catalysts known from the prior art for the preparation of VAM have for example catalyst supports based on silicon oxide, aluminium oxide, aluminosilicates, titanium oxide or zirconium oxide (cf. on this EP 839 793 A1, WO 98/018553 A1, WO 2000/058008 A1 and WO 2005/061107 A1). However, catalyst supports based on titanium oxide or zirconium oxide are currently rarely used, since these catalyst supports display no long-term resistance to acetic acid and are relatively expensive.

Most catalysts used at present for the preparation of VAM are shell catalysts with a Pd/Au shell on an oxidic porous catalyst support formed as a shaped body, for example a porous, amorphous aluminosilicate support in the form of a sphere based on natural, acid-treated calcined bentonites. The catalyst support is usually full impregnated with potassium acetate as a so-called promoter.

Such VAM shell catalysts are usually prepared by wet-chemical means, in which the catalyst support is loaded with corresponding solutions of metal precursor compounds, for example by dipping the support in the solutions or by means of the incipient wetness process (pore-filling process), in which the support is loaded with a volume of solution corresponding to its pore volume by steeping.

The Pd/Au shell of the catalyst can be produced for example by first steeping the catalyst support in a first step in a solution of a Pd salt, e.g. an $Na_2PdCl_4$ solution, and then in a subsequent second step fixing the Pd component by applying an NaOH solution onto the catalyst support in the form of its Pd-hydroxide compound. In a subsequent separate third step, the catalyst support can be steeped in a solution of a gold salt, e.g. an $NaAuCl_4$ solution, and the Au components are then likewise fixed by means of NaOH. After the fixing of the noble-metal components in an outer shell of the catalyst support, the loaded catalyst support is then very largely washed free of chloride and Na ions, then dried and finally reduced with ethylene at 150° C. The produced Pd/Au shell usually has a thickness of about 100 to 500 μm.

The catalyst support loaded with the noble metals is usually loaded with potassium acetate (the promoter) after the fixing and/or reducing step wherein, rather than the loading with potassium acetate taking place only in the outer shell loaded with noble metals, the catalyst support is completely impregnated through with the promoter. A Süd-Chemie AG spherical support called "KA-160" based on naturally occurring acid-treated calcined bentonites which has a BET surface area of approx. 160 m²/g can be used for example as catalyst support.

The selectivities in the preparation of VAM using the Pd/Au shell catalysts known from the state of the art are about 90 mol-%, relative to the ethylene used, wherein the remaining 10 mol-% of the reaction products substantially consist of $CO_2$ which is formed by total oxidation of the organic educts/products.

Various possibilities have been proposed to increase the activity of such shell catalysts, in particular the doping of the catalyst support or the shell with further promoter metals.

Thus U.S. Pat. No. 6,849,243 B1 describes, in addition to the use of $TiO_2$ as a constituent of the catalyst support, the use of barium and cadmium as additional promoter metal components. In particular, neodymium, titanium, magnesium, zirconium, yttrium, praseodymium, lanthanoids and rubidium and also their binary combinations are disclosed in US 2006/0135809 A1 as additional promoters in the shell of the shell catalyst.

Furthermore, the use of MoVNbX catalysts for the preparation of VAM is known from U.S. Pat. No. 6,605,739, wherein X is selected from phosphorus, boron, hafnium, tellurium, arsenic or mixtures thereof.

EP 1 102 635 B1 also teaches the use of one or more hafnium compounds which are arranged on the support, in particular in the shell of the shell catalyst, with the result that the catalytically active component conforms to the formula $Pd/Au/HfO_2$.

In particular the concepts of the three above-mentioned documents of introducing hafnium into the shell of the shell catalyst in addition to palladium and gold have proven to be ineffectual, in particular because of the inadequate solubility of hafnium compounds.

Furthermore, it has been established that although these catalysts have an increased activity in terms of VAM conversion compared with the previously known catalysts with a pure Pd/Au shell, their activity is increased only for a relatively short period of time and rapidly decreases again after a maximum.

It was therefore an object of the present invention to provide a new shell catalyst, in particular for the preparation of VAM, which is characterized by a high activity and VAM selectivity and which further retains the increased activity and selectivity over a long period of time.

This object is achieved by the provision of a shell catalyst, in particular for the preparation of vinyl acetate monomer (VAM), comprising an oxidic porous catalyst support with an outer shell, wherein the outer shell contains metallic Pd and Au and wherein the framework structure of the porous catalyst support contains hafnium oxide units ($HfO_2$).

By the expression "hafnium oxide units ($HfO_2$)" is meant here discrete hafnium oxide in particle form which adheres firmly to the framework structure of the catalyst support for example by sintering and thus forms an integral constituent of the framework structure of the support. A further possibility particularly preferred according to the invention is the replacement of for example silicon dioxide, aluminium oxide or $ZrO_2$ units of the corresponding support materials with $HfO_2$ units which can take the place of the $SiO_4$, $AlO_4$ or $ZrO_4$ tetrahedrons in the structure for example in the form of $HfO_4$ tetrahedrons and thus have a chemical bond to the framework structure and therefore are likewise an integral part of the framework structure. Thus, it is important according to the invention that $HfO_2$ in one or other form is an integral constituent of the framework structure.

The replacement of the framework constituents can be achieved by a person skilled in the art using methods known per se, for example already during the direct synthesis of such support materials or by solid ion exchange or liquid ion exchange, for example in the case of aluminosilicates.

The disadvantages of the hafnium oxide additions known hitherto are avoided by the integration of the hafnium oxide units into the framework structure of the support or into the support, instead of onto the support, as previously known from the prior art. The catalyst according to the invention is thereby characterized by a higher activity and higher VAM selectivity than the hafnium oxide-containing VAM catalysts known from the prior art. It maintains this activity and selectivity over long service lives.

The activity and selectivity were related to the conditions during the customary VAM preparation: usually, the reaction for the preparation of VAM is carried out in installations with a 45% oxygen conversion and the space-time yield (STY) of VAM (kg VAM per liter of catalyst per hour) is then measured.

A hafnium doping according to the invention leads to an increase in the STY of >5%, preferably even >10%. The activity advantage can further be transformed into a selectivity improvement of the catalyst according to the invention of >1% by a targeted adaptation of the surface area and porosity of the support (smaller surface area and larger pores). The rule is: the higher the $HfO_2$ doping is, the smaller the support surface area must be. Typical values are 20-40 $m^2/g$ (BET) for pure $HfO_2$ and about 60-120 $m^2/g$ (BET) for calcined acid-treated sheet silicates with an $HfO_2$ content (framework doping) of 0.01 to 50 wt.-%, preferably 0.01 to 25 wt.-%.

According to the invention, the oxidic porous catalyst support is either already formed per se as a homogeneous shaped body or is applied to a porous or non-porous shaped body of e.g. steatite, bentonite, aluminium dioxide, etc. or other suitable material, such as $ZrO_2$ or mixtures of these materials.

In the following, the terms "catalyst" and "shell catalyst" are used synonymously.

The hafnium oxide units are preferably evenly distributed in the framework structure of the catalyst support, but an uneven distribution in the framework structure is also provided for according to the invention.

By the term "evenly distributed" used above is meant either that the hafnium oxide units are homogeneously distributed, as already said, in corresponding form in the structure of the porous catalyst support as individual hafnium oxide units or groups of same or that the hafnium oxide is present in the structure of the catalyst support in the form of hafnium oxide particles which are evenly distributed in the framework structure of the catalyst support. In other words, the latter means that the framework structure of the catalyst support is formed of a solid structure of particles of porous oxidic catalyst support and hafnium oxide units sintered together. In the case of $ZrO_2$ which is framework-doped with $HfO_2$, $HfO_2$—$ZrO_2$ mixed oxides, which are preferred according to the invention, often are formed.

The expression "evenly distributed" used according to the invention consequently excludes catalyst supports where only the inner or the inner and outer surface of the porous catalyst support is covered or coated with the doping oxide or where the $HfO_2$ is concentrated only in an outer shell, such as is known from the above-cited prior art. Such catalyst supports are obtained for example by impregnating the surface of a porous oxidic catalyst support shaped body with a solution of a corresponding compound and then converting the compound into the corresponding oxide.

The catalyst support containing hafnium oxide units (in other words: the catalyst support doped with hafnium oxide) can be obtained for example by means of the following process, comprising the steps of:

a) mixing a powdery oxidic porous support material with a powdery hafnium compound and/or a solution or suspension of a hafnium salt;
b) shaping a shaped body from the mixture obtained according to step a);
c) calcining the shaped body obtained according to step b).

The hafnium compound is preferably converted into the oxide during the calcining, unless it is already hafnium oxide. Suitable hafnium compounds include, but are not limited to, $(NH_4)_2[HfF_6]$, $HfCl_4$, $HfO_2$, $HfI_3$, $HfCl_3$, $HfCl_2$, $HfOCl_2$, $HfO(NO_3)_2$, $HfO(OAc)_2$, $HfB_5$, $K_5[Hf(CN)_5]$, $[Hf(bipy)_3]$, $Hf(SO_4)_2$, $Na_2HfO_3$, $Na_4HfO_4$.

According to a preferred embodiment of the shell catalyst according to the invention it is provided that the porous oxidic catalyst support comprises or is constructed from a silicon oxide, aluminium oxide, aluminosilicate (e.g. zeolites), zirconium oxide, titanium oxide, a calcined acid-treated bentonite, very generally sheet silicates or a mixture of two or more of the above-named oxides. Pure zirconium dioxide and calcined bentonites/sheet silicates which contain up to 20 wt.-% $ZrO_2$ are particularly preferred.

It is quite particularly preferred if the hafnium oxide units are contained in the framework structure of the catalyst support in a proportion of 0.03 to 20 wt.-%, relative to the weight of the pure catalyst support. If the hafnium oxide units are present in the framework structure of the catalyst support in a proportion of less than 0.03 wt.-%, then the effect of the properties of the hafnium oxide which increase the activity of the shell catalyst according to the invention is only small, while above a proportion of 25 wt.-% the increase in the activity of the catalyst is accompanied by a clear decrease in VAM selectivity.

It has been established that, the smaller the surface area of the catalyst support, the higher the VAM selectivity of the shell catalyst according to the invention. In addition, the smaller the surface area of the catalyst support is, the greater the chosen thickness of the Pd/Au shell can be, without appreciable losses of VAM selectivity.

According to a preferred embodiment of the catalyst according to the invention, the specific surface area of the catalyst support has a value of less than/equal to 160 m²/g, preferably less than 140 m²/g, preferably less than 135 m²/g, further preferably less than 120 m²/g, more preferably less than 100 m²/g, still more preferably less than 80 m²/g and quite particularly preferably less than 65 m²/g.

By "specific surface area" of the catalyst support is meant within the framework of the present invention the BET surface area of the support which is determined by means of adsorption of nitrogen according to DIN 66132.

According to a quite particularly advantageous development of the shell catalyst according to the invention, it can be provided that the catalyst support has a specific surface area in the range of 160 to 40 m²/g, preferably between 140 and 50 m²/g, preferably between 135 and 50 m²/g, further preferably between 120 and 50 m²/g, quite particularly preferably between 100 and 50 m²/g.

According to the invention, "catalyst support" denotes either a shaped body made of the above-named materials or mixtures thereof or a layer which has been applied to a porous or non-porous shaped body e.g. in the form of a washcoat, i.e. an aqueous suspension of the above-named materials or mixtures thereof, and thus likewise forms a "shell". Functionally according to the invention, "catalyst support" thus means the part of the shell catalyst according to the invention that carries the metallic shell which contains the Pd/Au catalyst. In the present case it is clear from the context whether shaped bodies consisting of the porous catalyst support material are meant. Otherwise, "catalyst support" refers both to a shell containing or consisting of the catalyst support material and to a shaped body made of the materials.

The porous catalyst support shaped body of the catalyst according to the invention can be prepared for example on the basis of an iron oxide-doped, calcined, acid-treated bentonite by grinding a powdery (uncalcined) acid-treated bentonite with a powdery iron compound and/or an iron solution and also water and then mixing thoroughly until homogeneous. There are also naturally occurring bentonites which already contain iron as an impurity, from which a greater or lesser quantity of iron can be washed out with acid in order to prepare an iron-doped support, without having to add additional iron. The resulting mixture is shaped accompanied by compression to form a shaped body by means of devices familiar per se to a person skilled in the art, such as for example extruders or tablet presses, and the uncured shaped body is then calcined to form a stable shaped body. The calcining is preferably carried out at temperatures at which a solid structure is obtained and optionally the iron compound is converted into iron(III) oxide. The size of the specific surface area of the doped catalyst support depends in particular on the quality of the (untreated) bentonite used, the acid-treatment method of the bentonite used, i.e. for example the nature and the quantity, relative to the bentonite, and the concentration of the inorganic acid used, the acid-treatment duration and temperature, on the moulding pressure and on the calcining duration and temperature and also the calcining atmosphere.

Acid-treated bentonites can be obtained by treating bentonites with strong (Brønstedt) acids, such as for example sulphuric acid, phosphoric acid or hydrochloric acid. The definition, used within the framework of the present invention, of the term "bentonite" is given in: Römpp, Lexikon Chemie, 10$^{th}$ edition, Georg Thieme Verlag. Bentonites particularly preferred within the framework of the present invention are natural aluminium-containing sheet silicates which contain montmorillonite (in the form of smectite) as main mineral. After the acid treatment, the bentonite is normally washed with water, dried and ground to a powder.

The shell catalyst according to the invention is usually prepared by subjecting a plurality of shaped bodies to a batch process during the individual process steps of which the shaped bodies are for example subjected to relatively high mechanical load stresses communicated by stirring and mixing tools. In addition, the catalyst according to the invention can be subjected to a strong mechanical load stress during the filling of a reactor, which can result in an undesired formation of dust and damage to the catalyst support, in particular to its catalytically active shell lying in an outer area.

In particular to keep the abrasion of the catalyst according to the invention within reasonable limits, the catalyst support therefore preferably has a hardness greater than/equal to 20 N, preferably greater than/equal to 25 N, quite particularly preferably greater than/equal to 35 N and most preferably greater than/equal to 40 N. The hardness is ascertained in the present case by means of an 8M tablet-hardness testing machine from Dr. Schleuniger Pharmatron AG, determining the average for 99 shell catalysts after drying of the catalyst at 130° C. for 2 h, wherein the apparatus settings are as follows:

| | |
|---|---|
| Hardness: | N |
| Distance from the shaped body: | 5.00 mm |
| Time delay: | 0.80 s |
| Feed type: | 6 D |
| Speed: | 0.60 mm/s |

The hardness of the catalyst support can also be influenced for example by varying the process parameters during its preparation, for example through the selection of the support material and the type of hafnium starting material and also its quantity, the calcining duration and/or the calcining temperature of an uncured shaped body formed from a corresponding support mixture, or by particular optional loading materials, such as for example methyl cellulose or magnesium stearate.

The catalyst according to the invention therefore comprises a shaped body as an actual catalyst support, preferably based on a correspondingly doped, calcined acid-treated bentonite or on a mixed oxide based on zirconium oxide or mixtures thereof.

The expression "based on" means that in this case the catalyst according to the invention comprises a doped calcined acid-treated bentonite. It is preferred that the proportion of the calcined, acid-treated bentonite is greater than/equal to 50 wt.-%, preferably greater than/equal to 60 wt.-%, preferably greater than/equal to 70 wt.-%, further preferably greater than/equal to 80 wt.-%, relative to the weight of the catalyst support containing hafnium dioxide units.

It was found that the VAM selectivity of the catalyst according to the invention was raised when the integral pore volume of the catalyst support increases. According to a further preferred embodiment of the catalyst according to the invention, the catalyst support therefore has an integral pore volume according to BJH of more than 0.25 ml/g, preferably more than 0.30 ml/g, and most preferably more than 0.35 ml/g. In the case of pure $ZrO_2$, as a comparison, the pore volume lies in the range of 0.2-0.4 ml/g.

The integral pore volume of the catalyst support is determined according to the BJH method by means of nitrogen adsorption. The surface area of the catalyst support and its integral pore volume are determined according to the BET or according to the BJH method. The BET surface area is determined according to the BET method according to DIN 66131; a publication of the BET method is also found in J. Am. Chem. Soc. 60, 309 (1938). In order to determine the surface area and the integral pore volume of the catalyst support or the catalyst, the sample can be measured for example with a fully automatic nitrogen porosimeter from Micromeritics, type ASAP 2010, by means of which an adsorption and desorption isotherm is recorded.

To determine the surface area and the porosity of the catalyst support or the catalyst according to the BET process, the data are evaluated according to DIN 66131. The pore volume is determined from the measurement data using the BJH method (E. P. Barret, L. G. Joiner, P. P. Haienda, J. Am. Chem. Soc. 73 (1951, 373)). Effects of capillary condensation are also taken into account when using this method. Pore volumes of specific pore size ranges are determined by totaling incremental pore volumes which are obtained from the evaluation of the adsorption isotherms according to BJH. The integral pore volume according to the BJH method relates to pores with a diameter of 1.7 to 300 nm.

It is further advantageous according to a further preferred embodiment of the shell catalyst according to the invention if the water absorbency of the catalyst support is 40 to 75%, preferably 50 to 70% calculated as the weight increase due to water absorption. The absorbency is determined by steeping 10 g of the support sample in deionized water for 30 min until gas bubbles no longer escape from the support sample. The excess water is then decanted and the steeped sample blotted with a cotton towel to remove adhering moisture from the sample. The water-loaded support is then weighed and the absorbency calculated as follows:

(amount weighed out (g)−amount weighed in (g))× 10=water absorbency (%)

It is advantageous if the catalyst support has an integral pore volume according to BJH in the range of 0.25 to 0.7 ml/g, preferably in a range of 0.3 to 0.55 ml/g and quite particularly preferably in the range of 0.35 to 0.5 ml/g.

It is preferred according to a further preferred embodiment of the catalyst according to the invention that at least 80%, preferably at least 85% and preferably at least 90%, of the integral pore volume of the catalyst support according to BJH is formed by mesopores and macropores. This counteracts a reduced activity, effected by diffusion limitation, of the catalyst according to the invention, in particular with relatively thick Pd/Au shells. By micropores, mesopores and macropores are meant in this case pores which have a diameter of less than 1 nm, a diameter of 1 to 50 nm and a diameter of more than 50 nm respectively.

Likewise in view of a small pore diffusion limitation, it is preferred according to a further embodiment of the catalyst according to the invention that the catalyst support has an average pore diameter of 8 to 50 nm, preferably 9 to 20 nm and preferably 10 to 15 nm.

The catalyst according to the invention should preferably have a bulk density of more than 0.4 g/ml, preferably more than 0.45 g/ml and particularly preferably a bulk density of between 0.45 and 0.75 g/ml.

In order to ensure a sufficient chemical stability of the catalyst according to the invention, in the case that the support contains calcined acid-treated bentonite, it has an $SiO_2$ content of at least 65 mass-%, preferably at least 80 mass-% and preferably 95 to 99.5 mass-%, relative to the mass of the undoped calcined acid-treated bentonite.

In the gas-phase synthesis of VAM from acetic acid and ethene, a relatively low $Al_2O_3$ content in the calcined acid-treated bentonite is scarcely disadvantageous, whereas with high $Al_2O_3$ contents a marked reduction in indentation hardness must be expected. According to a preferred embodiment of the catalyst according to the invention, the acid-treated bentonite therefore contains less than 10 mass-% $Al_2O_3$, preferably 0.1 to 3 mass-% and preferably 0.3 to 1.0 mass-%, relative to the mass of the calcined acid-treated bentonite.

The acidity of the catalyst support advantageously influences the activity of the catalyst according to the invention during the gas phase synthesis of VAM from acetic acid and ethene. According to a further preferred embodiment of the catalyst according to the invention, the catalyst support has a Bayer acidity of between 1 and 150 µval/g, preferably between 5 and 130 µval/g and particularly preferably between 10 and 100 µval/g.

As already mentioned, the catalyst support of the catalyst according to the invention is preferably present as a so-called "shaped body". The catalyst support can in principle assume the form of any geometric body to which a shell, explained in detail below, which contains catalytically active metals can be applied. However, it is preferred if the catalyst support is formed as a sphere, cylinder (also with rounded end surfaces), perforated cylinder (also with rounded end surfaces), trilobe, "capped tablet", tetralobe, ring, doughnut, star, cartwheel, "reverse" cartwheel, or as a strand, preferably as a ribbed strand or star strand. The spherical shape is quite particularly preferred, since it can also be easily provided with a "shell".

The diameter or the length and thickness of the catalyst support of the catalyst according to the invention is preferably 2 to 9 mm, depending on the geometry of the reactor tube in which the catalyst is to be used. If the catalyst support is formed as a sphere, then the catalyst support preferably has a diameter of more than 2 mm, preferably a diameter of more than 3 mm and preferably a diameter of 4 mm to 9 mm.

In general, the smaller the thickness of the Pd/Au shell of the catalyst, the higher the VAM selectivity of the catalyst according to the invention. According to a further preferred embodiment of the catalyst according to the invention, the shell of the catalyst therefore has a thickness of less than 300 µm, preferably less than 200 µm, preferably less than 150 µm, further preferably less than 100 µm and still more preferably less than 80 µm.

The thickness of the shell can be measured visually by means of a microscope. The area in which the noble metals Pd/Au are deposited appears black, while the areas free of noble metals appear white. As a rule, the boundary between areas containing noble metals and areas free of them is very sharp and can clearly be recognized visually. If the above-named boundary is not sharply defined and accordingly not clearly recognizable visually, the thickness of the shell corresponds to the thickness of a shell, measured starting from the outer surface of the catalyst support, which contains 95% of the noble metal deposited on the support.

However, it was likewise found that in the case of the catalyst according to the invention, in particular the surface arms, the Pd/Au shell can be formed with a relatively large thickness effecting a high activity of the catalyst, without effecting an appreciable reduction of the VAM selectivity of the catalyst according to the invention. According to another, likewise preferred embodiment of the catalyst according to the invention, the shell of the catalyst therefore has a thickness in the range of 200 to 2000 μm, preferably in the range of 250 to 1800 μm, quite particularly preferably in the range of 300 to 1500 μm and further preferably in the range of 400 to 1200 μm.

In order to ensure an adequate activity of the catalyst according to the invention, the proportion of Pd in the catalyst is 0.5 to 2.5 wt.-%, preferably 0.6 to 2.3 wt.-% and preferably 0.7 to 2 wt.-%, relative to the weight of the catalyst support loaded with noble metal.

It can also be preferred if the catalyst according to the invention has a Pd content of 1 to 20 g/l, preferably 2 to 15 g/l and preferably 3 to 10 g/l.

In order to likewise ensure an adequate activity and selectivity of the catalyst according to the invention, the Au/Pd atomic ratio of the catalyst is preferably between 0 and 1.2, preferably between 0.1 and 1, preferably between 0.3 and 0.9 and particularly preferably between 0.4 and 0.8.

In addition it can be preferred if the catalyst according to the invention has an Au content of 1 to 20 g/l, preferably 1.5 to 15 g/l and preferably 2 to 10 g/l.

In order to ensure a largely uniform activity of the catalyst according to the invention over the thickness of the Pd/Au shell, the noble-metal concentration should vary only relatively little over the shell thickness. This means that, over an area of 90% of the shell thickness, the area being at a distance of 5% of the shell thickness from each of the outer and inner shell limit, the profile of the noble-metal concentration of the catalyst from the average noble-metal concentration of this area varies by a maximum of +/−20%, preferably by a maximum of +/−15% and preferably by a maximum of +/−10%.

In further preferred embodiments, hafnium oxide units are likewise present additionally in the shell of the catalyst according to the invention, preferably in a quantity of 0.1-20 wt.-%, relative to the weight of the whole catalyst.

Furthermore, the shell can also contain zirconium dioxide, wherein the zirconium dioxide content is in the range of 10 to 20 wt.-%, relative to the weight of the whole catalyst.

Chloride poisons the catalyst according to the invention and leads to a deactivation of same. According to a further preferred embodiment of the catalyst according to the invention, its chloride content is therefore less than 250 ppm, preferably less than 150 ppm.

The catalyst according to the invention preferably contains, in addition to the hafnium oxide, at least one alkali metal compound as a further promoter, preferably a potassium, sodium, caesium or rubidium compound, preferably a potassium compound. Suitable and particularly preferred potassium compounds include potassium acetate KOAc, potassium carbonate $K_2CO_3$, potassium hydrogen carbonate $KHCO_3$ and potassium hydroxide KOH and also all potassium compounds which become potassium acetate (KOAc) under the respective reaction conditions of VAM synthesis. The potassium compound can be deposited on the catalyst support both before and after the reduction of the metal components into the metals Pd and Au. According to a further preferred embodiment of the catalyst according to the invention, the catalyst comprises an alkali metal acetate, preferably potassium acetate.

It is particularly preferred in order to ensure an adequate promoter activity if the alkali metal acetate content of the catalyst is 0.1 to 0.7 mol/l, preferably 0.3 to 0.5 mol/l.

According to a further preferred embodiment of the catalyst according to the invention, the alkali metal/Pd atomic ratio is between 1 and 12, preferably between 2 and 10 and particularly preferably between 4 and 9. Preferably, the smaller the surface area of the catalyst support, the lower the alkali metal/Pd atomic ratio.

The present invention further also relates to a process for the preparation of a shell catalyst according to the invention, comprising the steps of:
a) providing an oxidic porous catalyst support, the framework structure of which contains hafnium oxide ($HfO_2$) units.
b) depositing a solution of a Pd precursor compound onto the catalyst support;
c) depositing a solution of an Au precursor compound onto the catalyst support the framework structure of which contains hafnium oxide units ($HfO_2$);
d) converting the Pd component of the Pd precursor compound into the metal form;
e) converting the Au component of the Au precursor compound into the metal form.

In principle, any Pd or Au compound by means of which a high degree of dispersion of the metals can be achieved can be used as Pd and Au precursor compound. By "degree of dispersion" is meant the ratio of the number of all the surface metal atoms of all the metal/alloy particles of a supported metal catalyst to the total number of all the metal atoms of the metal/alloy particles. In general it is preferred if the degree of dispersion corresponds to a relatively high numerical value, since in this case as many metal atoms as possible are freely accessible for a catalytic reaction.

This means that, given a relatively high degree of dispersion of a supported metal catalyst, a specific catalytic activity of same can be achieved with a relatively small quantity of metal used. According to a further preferred embodiment of the catalyst according to the invention, the degree of dispersion of the metal particles is 1 to 20%. The values of the degree of dispersion are determined by means of CO adsorption.

It is preferred to select the Pd and Au precursor compounds from the halides, in particular chlorides, oxides, nitrates, nitrites, formates, propionates, oxalates, acetates, hydroxides, hydrogen carbonates, amine complexes or organic complexes, for example triphenylphosphane complexes or acetylacetonate complexes, of these metals.

Examples of particularly preferred Pd precursor compounds are water-soluble Pd salts. According to particularly preferred embodiments of the process according to the invention, the Pd precursor compounds are selected from the group consisting of $Pd(NH_3)_4(OH)_2$, $Pd(NO_3)_2$, $K_2Pd(OAc)_2(OH)_2$, $Pd(NH_3)_2(NO_2)_2$, $Pd(NH_3)_4(NO_3)_2$, $K_2Pd(NO_2)_4$, $Na_2Pd(NO_2)_4$, $Pd(OAc)_2$, $PdCl_2$ and $Na_2PdCl_4$ and $H_2PdCl_4$ and $K_2PdCl_4$ and $(NH_4)_2PdCl_4$ and $Pd(NH_3)_4Cl_2$ and $Pd(NH_3)_4(HPO_4)$ and ammonium Pd oxalate and Pd oxalate and $K_2Pd(C_2O_4)_2$ and Pd(II) trifluoroacetate. In addition to $Pd(OAc)_2$ other carboxylates of palladium can also be used, preferably the salts of the aliphatic monocarboxylic acids with 3 to 5 carbon atoms, for example the propionate or butyrate salt.

According to a further preferred embodiment of the process according to the invention, Pd nitrite precursor compounds can also be preferred. Preferred Pd nitrite precursor compounds are for example those which are obtained by dissolving $Pd(OAc)_2$ in an $NaNO_2$ solution.

Examples of preferred Au precursor compounds are water-soluble Au salts. According to a particularly preferred embodiment of the process according to the invention, the Au precursor compound is selected from the group consisting of $KAuO_2$, $HAuCl_4$, $NaAuO_2$, $KAu(NO_2)_4$, $AuCl_3$, $NaAuCl_4$, $KAuCl_4$, $(Nh4)AuCl_4$, $KAu(OAc)_3(OH)$, $NaAu(OAc)_3(OH)$, $HAu(NO_3)_4$ and $Au(OAc)_3$. It is recommended where appropriate to prepare fresh Au(OAc)$_3$ or KAuO$_2$ each time by precipitating the oxide/hydroxide from a gold acid solution, washing and isolating the precipitate and taking up same in acetic acid or KOH.

All solvents in which the selected precursor compounds are soluble and which, after deposition onto the catalyst support, can be easily removed again from same by means of drying are suitable as solvents for the precursor compounds. Preferred solvent examples for the metal acetates as precursor compounds are in particular unsubstituted carboxylic acids, in particular acetic acid, and for the metal chlorides in particular water or dilute hydrochloric acid.

If the precursor compounds are not sufficiently soluble in acetic acid, water or dilute hydrochloric acid or mixtures thereof, other solvents can also be used as an alternative or in addition to the named solvents. Solvents which are inert and miscible with acetic acid or water preferably come into consideration as other solvents in this case. Ketones, for example acetone or acetylacetone, furthermore ethers, for example tetrahydrofuran or dioxan, acetonitrile, dimethylformamide and solvents based on hydrocarbons such as for example benzene may be named as preferred solvents which are suitable for adding to acetic acid, but may also be used in other embodiments as the only solvent.

Ketones, for example acetone, or alcohols, for example ethanol or isopropanol or methoxyethanol, lyes, such as aqueous KOH or NaOH, or organic acids, such as acetic acid, formic acid, citric acid, tartaric acid, malic acid, glyoxylic acid, glycolic acid, oxalic acid, pyruvic acid or lactic acid may be named as preferred solvents which are suitable for adding to water, but may also be used in other embodiments as the only solvent.

If chloride compounds are used as precursor compounds, it must be ensured that the chloride ions are reduced to a tolerable residual quantity before using the catalyst prepared according to the process according to the invention, since chloride is a catalyst poison. For this, the catalyst support is as a rule washed with plenty of water after the fixing of the Pd and Au components of the Pd or Au precursor compound onto the catalyst support. In general, this happens either immediately after the fixing by hydroxide precipitation of the Pd and Au component by means of lye or after the reduction of the noble-metal components to the respective metal/alloy.

However, according to a preferred embodiment of the process according to the invention, chloride-free Pd and Au precursor compounds are used as well as chloride-free solvents to keep the chloride content in the catalyst as low as possible and avoid a laborious chloride-free washing. The corresponding acetate compounds are preferably used as precursor compounds, since they contaminate the catalyst support with chloride to only a very small extent.

The deposition of the Pd and Au precursor compounds onto the catalyst support in the area of an outer shell of the catalyst support can be achieved according to processes known per se. Thus the precursor solutions can be deposited by steeping, by dipping the support into the precursor solutions or steeping it according to the incipient wetness method. A base, for example caustic soda solution or potash lye, is then deposited on the catalyst support, whereby the noble-metal components are precipitated onto the support in the form of hydroxides. It is also possible for example to firstly steep the support in lye and then apply the precursor compounds to the thus-pretreated support. The same applies if hafnium oxide is additionally present in the shell, wherein water-soluble hafnium compounds are again preferably used.

According to a further preferred embodiment of the process according to the invention, it is therefore provided that the Pd and Au precursor compound is deposited on the catalyst support by steeping the catalyst support in the solution of the Pd precursor compound and in the solution of the Au precursor compound or in a solution which contains both the Pd and the Au precursor compound.

According to the state of the art, the active metals Pd and Au and also optionally Hf, starting from chloride compounds in the area of a shell of the support, are applied to same by means of steeping. However, this technique has reached its limits as regards minimum shell thicknesses and maximum Au loading and maximum Hf loading. The shell thickness of the corresponding known VAM catalysts is approx. 100 µm and it is not foreseen that even thinner shells can be obtained by means of steeping. In addition, higher Au loadings within the desired shell by means of steeping can be achieved only with difficulty, since the Au precursor compounds tend to diffuse from the shell into inner zones of the catalyst support shaped body, which results in broad Au shells, areas of which contain very little Pd.

The active metals, or, put a better way, their precursor compounds, can also be deposited on the support for example by means of so-called physical processes. For this, the support according to the invention can preferably be sprayed for example with a solution of the precursor compounds, wherein the catalyst support is moved in a coating drum into which hot air is blown, with the result that the solvent quickly evaporates.

According to a further preferred embodiment of the process according to the invention, it is provided that the solution of the Pd precursor compound and the solution of the Au precursor compound is deposited onto the catalyst support by spraying the solutions onto a fluid bed or a fluidized bed of the catalyst support, preferably by means of an aerosol of the solutions. The shell thickness can thereby be continuously adjusted and optimized, for example up to a thickness of 2 mm. But even very thin shells with a thickness of less than 100 µm are thus possible.

The above-named embodiment of the process according to the invention can be carried out using a fluid bed or fluidized bed unit. It is particularly preferred if the unit contains a so-called controlled air-glide layer. For one thing, the catalyst support shaped bodies are thoroughly mixed by the controlled air-glide layer, wherein they simultaneously rotate about their own axis, whereby they are dried evenly by the process air. For another, due to the consequent orbital movement, effected by the controlled air-glide layer, of the shaped bodies the catalyst support shaped bodies pass through the spray procedure (application of the precursor compounds) at a virtually constant frequency.

A largely uniform shell thickness of a treated batch of shaped bodies is thereby achieved. A further result is that the noble-metal concentration varies only relatively slightly over a relatively large area of the shell thickness, i.e. such that the noble-metal concentration describes an approximately rectangular function over a large area of the shell thickness, whereby a largely uniform activity of the resulting catalyst is ensured over the thickness of the Pd/Au shell. Suitable coating drums, fluid bed units and fluidized bed units for carrying out the process according to the invention according to preferred embodiments are known in the state of the art and sold e.g. by Heinrich Brucks GmbH (Alfeld, Germany), ERWEK GmbH (Heusenstamm, Germany), Stechel (Germany), DRIAM Anlagenbau GmbH (Eriskirch, Germany), Glatt GmbH (Binzen, Germany), G.S. Divisione Verniciatura (Osteria, Italy), HOFER-Pharma Maschinen GmbH (Weil am Rhein, Germany), L.B. Bohle Maschinen+Verfahren GmbH (Enningerloh, Germany), Lödige Maschinenbau GmbH (Paderborn, Germany), Manesty (Merseyside, United Kingdom), Vector Corporation (Marion, Iowa, USA), Aeromatic-Fielder AG (Bubendorf, Switzerland), GEA Process Engineering (Hampshire, United Kingdom), Fluid Air Inc. (Aurora, Ill., USA), Heinen Systems GmbH (Varel, Germany), Hüttlin GmbH (Steinen, Germany), Umang Pharmatech Pct Ltd. (Marharashtra, India) and Innojet Technologies (Lörrach, Germany).

According to a further preferred embodiment of the process according to the invention, the catalyst support is heated during the deposition of the solutions, for example by means of heated process air. The drying-off speed of the deposited solutions of the noble-metal precursor compounds can be determined via the degree of heating of the catalyst supports. At relatively low temperatures the drying-off speed is for example relatively low, with the result that with a corresponding quantitative deposition, greater shell thicknesses can be formed because of the high diffusion of the precursor compounds that is caused by the presence of solvent. At relatively high temperatures the drying-off speed is for example relatively high, with the result that solution of the precursor compounds coming into contact with the shaped body almost immediately dries off, which is why solution deposited on the catalyst support cannot penetrate deep into the latter. At relatively high temperatures such relatively small shell thicknesses can thus be obtained with a high noble-metal loading.

With the process described from the state of the art for the preparation of VAM shell catalysts based on Pd and Au commercially available solutions of the precursor compounds such as $Na_2PdCl_4$, $NaAuCl_4$ or $HAuCl_4$ solutions are customarily used. In the more recent literature, as already stated previously, chloride-free Pd or Au precursor compounds such as for example $Pd(NH_3)_4(OH)_2$, $Pd(NH_3)_2(NO_2)_2$ and $KAuO_2$ are also used. These precursor compounds react basic in solution, while the standard chloride, nitrate and acetate precursor compounds all react acid in solution.

To deposit the precursor compounds onto the catalyst support, preferably aqueous $Na_2PdCl_4$ and $NaAuCl_3$ solutions are customarily used. These metal-salt solutions are normally applied to the support at room temperature and the metal components then fixed with NaOH as insoluble Pd or Au hydroxides. Then the loaded support is customarily washed free of chloride with water. In particular the Au fixing has disadvantages, such as long action times of the base in order to induce the precipitation of the stable Au tetrachloro complex, incomplete precipitation and concomitant inadequate Au retention.

According to a further preferred embodiment of the process according to the invention, the process comprises the steps in which
a) a first solution of a Pd and/or an Au precursor compound is provided;
b) a second solution of a Pd and/or an Au precursor compound is provided, wherein the first solution effects a precipitation of the noble-metal component(s) of the precursor compound(s) of the second solution and vice versa;
c) the first solution and the second solution are deposited onto the catalyst support.

This embodiment of the process according to the invention uses two different precursor solutions, of which for example one contains a Pd and the other an Au precursor compound.

Generally, one of the solutions preferably has a basic, and the other an acidic pH. Generally, the solutions are deposited onto the catalyst support by firstly impregnating the support with the first and then in a subsequent step with the second solution, as described previously, by steeping. Upon deposition of the second solution the two solutions are then combined on the support, whereby the pH of the solutions changes and the Pd or Au component of the respective precursor compound is precipitated onto the support, without an auxiliary base, customary in the state of the art, such as NaOH or KOH, needing to be applied to the support.

The above embodiment of the process according to the invention is thus based on an impregnation of the catalyst support with the first solution of a Pd and/or Au precursor compound and the second solution of a Pd and/or Au precursor compound, wherein the two solutions are incompatible with one another, i.e. the first solution effects a precipitation of the noble-metal component(s) of the precursor compound(s) of the second solution and vice versa, with the result that in the contact zone of the two solutions both the pre-impregnated Pd/Au component(s) and the post-impregnated Pd/Au component(s) precipitate almost simultaneously and thus lead to an intimate thorough mixing of Pd/Au. Drying can optionally take place between the two impregnation steps.

Suitable aqueous solutions of Pd precursor compounds for the impregnation with incompatible solutions are listed by way of example in Table 1.

TABLE 1

| Precursor compound | Character of the solution |
| --- | --- |
| $PdCl_2$ | acidic |
| $Pd(NH_3)_2(NO_2)_2$ | basic |
| $Na_2PdCl_4$ | neutral |
| $Pd(NH_3)_4(OH)_2$ | basic |
| $Pd(NO_3)_2$ | acidic |
| $K_2Pd(OAc)_2(OH)_2$ | basic through dissolution of palladium acetate in KOH |

If, with regard to a premature Au reduction, $NH_3$ were to have too strong a reductive effect, the corresponding diamine complexes can also be used with ethylenediamine as ligand or the complexes with ethanol amine as ligand instead of the palladium amine complexes.

Suitable aqueous solutions of Au precursor compounds for the impregnation with incompatible solutions are listed by way of example in Table 2.

TABLE 2

| Precursor compound | Character of the solution |
| --- | --- |
| $AuCl_3$ | acidic |
| $KAuO_2$ | basic through dissolution of $Au(OH)_3$ in KOH |
| $NaAuCl_4$ | neutral |
| $HAuCl_4$ | acidic |
| $KAu(OAc)_3(OH)$ | basic through dissolution of $Au(OAc)_3$ in KOH |
| $HAu(NO_3)_4$ | acidic (stable in semi-concentrated $HNO_3$) |

Suitable combinations of incompatible solutions for the base-free precipitation of the noble-metal components are for example a $PdCl_2$ and a $KAuO_2$ solution; a $Pd(NO_3)_2$ and a $KAuO_2$ solution; a $Pd(NH_3)_4(OH)_2$ and an $AuCl_3$ or $HAuCl_4$ solution.

According to a further preferred embodiment of the process according to the invention, Pd can also be precipitated with incompatible Pd solutions and analogously Au with incompatible Au solutions, e.g. by bringing a $PdCl_2$ solution into contact with a $Pd(NH_3)_4(OH)_2$ solution or an $HAuCl_4$ with a $KAuO_2$ solution. In this way high Pd and/or Au contents can precipitate in the shell without having to use highly-concentrated solutions.

According to a further embodiment of the process according to the invention mixed solutions compatible with one another can also be used which are brought into contact with a solution incompatible with the mixed solution, for the noble-metal precipitation. An example of a mixed solution is a $PdCl_2$ and $AuCl_3$-containing solution, the noble-metal components of which can be precipitated with a $KAuO_2$ solution, or a $Pd(NH_3)_4(OH)_2$ and $KAuO_2$-containing solution, the noble-metal components of which can be precipitated with a $PdCl_2$ and $HAuCl_4$-containing solution. A further example of a mixed solution is the $HAuCl_4$ and $KAuO_2$ pairing.

The impregnation with the incompatible solutions will preferably take place by means of steeping or by means of spray impregnation, wherein the incompatible solutions are for example sprayed simultaneously by one or more double nozzle(s) or simultaneously by means of two nozzles or nozzle groups or sequentially by means of one or more nozzle(s).

Because of the rapid immobilization (fixing) of the metal components of the precursor compounds in the shell and the concomitant shortened Pd and Au diffusion, the impregnation with the incompatible solutions can lead to thinner shells than the conventional use of solutions compatible with one another. By means of the incompatible solutions, high noble-metal contents in thin shells, improved metal retention, more rapid and more complete precipitation of the noble metals, the reduction of the disruptive residual Na content of the support, the simultaneous fixing of Pd and Au in only one fixing step and the absence of NaOH costs and NaOH handling and an avoidance of a mechanical weakening of the support through the contact with excess NaOH can be achieved.

By means of the impregnation with incompatible solutions, greater noble-metal contents can be precipitated on the catalyst support through a single fixing step which comprises just the deposition of two incompatible solutions than is possible with standard base (NaOH) fixing. Shell catalysts with particularly low residual Cl and Na contents can be obtained by acid fixing of chloride-free noble metal precursors.

In particular, high Au contents with an Au/Pd atomic ratio of 0.6 and more, which is very desirable with regard to the increase in VAM selectivity, can be easily achieved by means of the principle of the incompatible solutions.

According to a further preferred embodiment of the process according to the invention it is provided that, after the Pd and/or the Au precursor compound has/have been deposited onto the catalyst support, for the fixing of the noble-metal component(s) of the precursor compound(s) onto the catalyst support, the catalyst support is subjected to a fixing step. The fixing step can comprise, as already stated above, the treatment of the support with lye or a calcining of the support for converting the noble-metal component(s) into a hydroxide compound(s) or into an oxide. The fixing step can also be omitted and directly reduced, e.g. in the gas phase.

It is likewise possible to introduce the doped catalyst support as powder and to impregnate this through with the precursor compounds of the active metals. The pre-treated powder can then be coated in the form of a washcoat onto a suitable shaped body, for example a sphere of steatite or a KA-160 support, and then processed further into the catalyst by calcining and reduction.

Accordingly the invention relates to a second process for the preparation of a shell catalyst according to the invention, comprising the steps of:
a) providing a powdery oxidic porous catalyst support which contains hafnium oxide ($HfO_2$) units in its framework structure and wherein the catalyst support is loaded with a Pd and an Au precursor compound or with Pd and Au particles;
b) depositing the loaded catalyst support onto a shaped body in the form of a shell;
c) calcining the loaded shaped body according to step b);
d) optionally converting the Pd and the Au component of the Pd or Au precursor compound into the metal form.

Alternatively, the named process can also be carried out by first depositing the powdery catalyst support not loaded with noble metal onto a shaped body and only afterwards applying the noble metals.

After loading with the precursor compounds or after fixing the noble-metal components the support can be calcined to convert the noble-metal components into the corresponding oxides. Calcining takes place preferably at temperatures of less than 700° C. Particularly preferably between 300-450° C. accompanied by the addition of air. The calcining time depends on the calcining temperature and is preferably chosen in the range from 0.5-6 hours. At a calcining temperature of approx. 400° C., the calcining time is preferably 1-2 hours. At a calcining temperature of 300° C., the calcining time is preferably up to 6 hours.

The noble-metal components are typically further reduced before the use of the catalyst, wherein the reduction can be carried out in situ, i.e. in the process reactor, or also ex situ, i.e. in a special reduction reactor. Reduction in situ is preferably carried out with ethylene (5 vol.-%) in nitrogen at a temperature of approx. 150° C. over a period of for example 5 hours. Reduction ex situ can be carried out for example with 5 vol.-% hydrogen in nitrogen, for example by means of forming gas, at temperatures in the range of preferably 150-500° C. over a period of 5 hours.

Gaseous or vaporable reducing agents such as for example CO, $NH_3$, formaldehyde, methanol and hydrocarbons can likewise be used, wherein the gaseous reducing agents can also be diluted with inert gas, such as for example carbon dioxide, nitrogen or argon. A reducing agent diluted with inert gas is preferably used. Mixtures of hydrogen with nitrogen or argon, preferably with a hydrogen content between 1 vol.-% and 15 vol.-%, are preferred.

The reduction of the noble metals can also be undertaken in the liquid phase, preferably by means of the reducing agents hydrazine, K-formate, $H_2O_2$ or Na-hypophosphite, K-hypophosphite, hypophosphoric acid.

The quantity of reducing agent is preferably chosen such that during the treatment period at least the equivalent required for complete reduction of the noble-metal components is passed over the catalyst. Preferably, however, an excess of reducing agent is passed over the catalyst in order to ensure a rapid and complete reduction.

The reduction is preferably pressureless, i.e. at an absolute pressure of approx. 1 bar. For the preparation of industrial quantities of catalyst according to the invention a rotary tube oven or fluid-bed reactor is preferably used in order to ensure an even reduction of the catalyst.

The invention also relates to the use of the catalyst according to the invention as an oxidation catalyst, as a hydrogenation/dehydrogenation catalyst, as a catalyst in hydrogenating desulphurization, as a hydrodenitrification catalyst, as a hydrodeoxidation catalyst or as a catalyst in the synthesis of alkenylalkanoates, in particular in the synthesis of vinyl acetate monomer, in particular in the gas-phase oxidation of ethylene and acetic acid to form vinyl acetate monomer.

The catalyst according to the invention is preferably used for the preparation of VAM. Generally this takes place by passing acetic acid, ethylene and oxygen or oxygen-containing gases over the catalyst according to the invention at temperatures of 100-200° C., preferably 120-200° C., and at pressures of 1-25 bar, preferably 1-20 bar, wherein non-reacted educts can be recycled. Expediently, the oxygen concentration is kept below 10 vol.-%. Under certain circumstances, however, a dilution with inert gases such as nitrogen or carbon dioxide is also advantageous.

Carbon dioxide is particularly suitable for dilution, since it is formed in small quantities in the course of VAM synthesis. The formed vinyl acetate is isolated with the help of suitable methods, which are described for example in U.S. Pat. No. 5,066,365 A.

The following embodiment examples serve to explain the invention but are not to be understood as limiting it:

EXAMPLE 1

500 g of different acid-treated dried powdery bentonite mixtures as sheet silicate component based on natural bentonites with montmorillonite as main constituent were ground into an intimate mixture by means of a ball mill with up to 100 g $ZrO_2$ and 10 g HfO2, and also 13 g methyl cellulose customary in the trade.

The resultant mixture was taken up with water and processed by means of a mixer into a dough from which spherical shaped bodies were prepared under pressure by means of a tablet press. For hardening, the spheres were calcined at a temperature of 640° C. over a period of 4 h. The thus-obtained shaped bodies have the characteristics listed in Table 3:

TABLE 3

Properties of shaped bodies according to the invention

| | |
|---|---|
| Geometric form | Sphere |
| Diameter | 5 mm |
| Moisture content | <2.0 mass-% |
| Compressive strength | >30N |
| Bulk density | 580-680 g $l^{-1}$ |
| Water absorbency | 54-70% |
| Specific surface area (BET) | 102-164 $m^2 g^{-1}$ |
| $SiO_2$ content | 70 to 78 wt.-% |
| $HfO_2$ content | 1.2-1.6 wt.-% |
| $ZrO_2$ content | 3.4 to 9.2 wt.-% |
| Other oxides | Residual mass in wt.-% |
| Loss on ignition 1000° C. | <0.4 wt.-% |
| Acidity | 10 to 50 µval/g |
| BJH pore volume $N_2$ | 0.25-0.42 $cm^3 g^{-1}$ |

A fluidized-bed device customary in the trade was filled with 225 g of the spheres, prepared as above, with a surface area of 122 $m^2$/g and the spheres were put into a fluidized-bed state by means of compressed air temperature-controlled at 80° C. (6 bar).

Once the shaped bodies were temperature-controlled at about 75° C., 300 ml of an aqueous noble-metal mixed solution containing 7.5 g $Na_2PdCl_4$ (sodium tetrachloropalladate) customary in the trade and 4.6 g $NaAuCl_4$ (sodium tetrachloroaurate) customary in the trade were sprayed onto the fluidized bed of the shaped bodies over a period of 40 min.

After the impregnation of the catalyst supports with the noble-metal mixed solution the support spheres were sprayed with a 0.05 molar NaOH solution in the fluidized-bed state under the above conditions over a period of 30 min. The NaOH was allowed to act on the shaped bodies for 16 h.

Following exposure to the action of the NaOH, the supports were washed with plenty of water in the fluidized-bed device, in order to very largely remove the alkali metal and chloride introduced into the support via the noble-metal compounds and NaOH.

After washing, the shaped bodies were dried in the fluidized-bed device at a temperature of 200 to 250° C.

After the shaped bodies were dried they were reduced to a Pd/Au shell catalyst with a gas mixture of ethylene (5 vol.-%) in nitrogen at a temperature of about 150° C. in the fluidized-bed device.

The resulting shell catalyst contained about 1.2 mass-% Pd and had an Au/Pd atomic ratio of about 0.5, a shell thickness of about 170 µm and a hardness of 37 N.

The noble-metal concentration of the thus-prepared Pd/Au shell catalyst varied over an area of 90% of the shell thickness, the area being at a distance of 5% of the shell thickness from each of the outer and inner shell limit, from the average noble-metal concentration of this area by a maximum of +/−10%.

EXAMPLE 2

50 g of $ZrO_2$ powder with a specific surface area of 39 $m^2$/g was mixed with 8 g powdery $HfO_2$ and ground to an intimate mixture by means of a ball mill. The resulting average particle size was about 2 µm.

The thus-obtained $HfO_2/ZrO_2$ powder has the characteristics listed in Table 4:

TABLE 4

Properties of the $HfO_2/ZrO_2$ powder

| | |
|---|---|
| Geometric form | Sphere |
| D50 | 2 µm |
| Moisture content | <2.0 wt.-% |
| Bulk density | 620 g $l^{-1}$ |
| Water absorbency | |
| Specific surface area (BET) | 39 $m^2$/g |
| $HfO_2$ content | 11.1% |
| $ZrO_2$ content | 88.8 wt.-% |
| Loss on ignition 1000° C. | <1 wt.-% |
| BJH pore volume $N_2$ | 0.28 $cm^3 g^{-1}$ |

30 g of a 20% zirconium acetate $ZrO(OAc)_2$ solution as binder was added to the $HfO_2/ZrO_2$ powder, the mixture was stirred for 1 h and then sprayed onto 75 g KA-0 (Süd-Chemie). The thus-obtained spheres were calcined at 600° C. for 5 h. An $HfO_2/ZrO_2$ shell of 261 µm resulted.

A fluidized-bed device customary in the trade was filled with 225 g of the spheres, prepared as above, with a surface area of 97 m2/g and the spheres were put into a fluidized-bed state by means of compressed air temperature-controlled to 80° C. (6 bar).

Once the shaped bodies were temperature-controlled at approx. 75° C., 300 ml of an aqueous noble-metal mixed solution containing 7.5 g $Na_2PdCl_4$ (sodium tetrachloropalladate) customary in the trade and 4.6 g $NaAuCl_4$ (sodium tetrachloroaurate) customary in the trade were sprayed onto the fluidized bed of the shaped bodies over a period of 40 min.

After the impregnation of the catalyst supports with the noble-metal mixed solution the support spheres were sprayed with a 0.05 molar NaOH solution in the fluidized-bed state under the above conditions over a period of 30 min. The NaOH was allowed to act on the shaped bodies for 16 h.

Following exposure to the action of the NaOH, the supports were washed with plenty of water in the fluidized-bed device, in order to very largely remove the alkali metal and chloride introduced into the support via the noble-metal compounds and NaOH.

After washing, the shaped bodies were dried in the fluidized-bed device at a temperature of 200 to 250° C.

After the shaped bodies were dried they were reduced to a Pd/Au shell catalyst with a gas mixture of ethylene (5 vol.-%) in nitrogen at a temperature of about 150° C. in the fluidized-bed device.

The resulting shell catalyst contained about 1.2 mass-% Pd and had an Au/Pd atomic ratio of about 0.5, a shell thickness of about 210 µm and a hardness of 43 N.

The noble-metal concentration of the thus-prepared Pd/Au shell catalyst varied over an area of 90% of the shell thickness, the area being at a distance of 5% of the shell thickness from each of the outer and inner shell limit, from the average noble-metal concentration of this area by a maximum of +/−10%.

The invention claimed is:

1. A shell catalyst for the preparation of vinyl acetate monomer (VAM), comprising an oxidic porous catalyst support with an outer shell, the shell containing metallic Pd and Au, wherein the porous catalyst support has a framework structure that contains hafnium oxide units ($HfO_2$).

2. The shell catalyst according to claim 1, wherein the catalyst support is selected from the group consisting of silicon oxides, aluminum oxides, aluminosilicates, zirconium oxide, titanium oxide, calcined acid-treated bentonites and mixtures thereof.

3. The shell catalyst according to claim 2, wherein the framework structure of the catalyst support has from 0.01 to 50 wt.-%, relative to the weight of the catalyst support, of hafnium oxide units.

4. The shell catalyst according to claim 3, wherein the catalyst support has a specific surface area (BET) of less than/equal to 160 $m^2/g$.

5. The shell catalyst according to claim 4, wherein the specific surface area (BET) of the catalyst support is in the range of 160 to 40 $m^2/g$.

6. The shell catalyst according to claim 5, wherein the catalyst support has a hardness greater than/equal to 20 N.

7. The shell catalyst according to claim 6, wherein the catalyst support has an integral BJH pore volume of more than 0.25 ml/g.

8. The shell catalyst according to claim 7, wherein the catalyst support has an integral BJH pore volume in the range of 0.25 to 0.7 ml/g.

9. The shell catalyst according to claim 8, wherein the catalyst support has an average pore diameter of 8 to 50 nm.

10. The shell catalyst according to claim 9, wherein the catalyst support has a Bayer acidity in the range of 1 to 150 µval/g.

11. The shell catalyst according to claim 1, wherein the catalyst support comprises a calcined acid-treated bentonite, preferably in a proportion of more than/equal to 50 wt.-%, relative to the weight of the catalyst support.

12. The shell catalyst according to claim 11, wherein the calcined acid-treated bentonite contained in the catalyst support has an $SiO_2$ content of at least 65 wt.-%.

13. The shell catalyst according to claim 12, wherein the calcined acid-treated bentonite contained in the catalyst support contains less than 10 wt.-% $Al_2O_3$.

14. The shell catalyst according to claim 1, wherein the catalyst support consists of $ZrO_2$.

15. The shell catalyst according to claim 1, wherein the catalyst support is applied to a porous or non-porous shaped body which is different from the catalyst support.

16. The shell catalyst according to claim 1, wherein the catalyst has a bulk density of more than 0.4 g/ml.

17. The shell catalyst according to claim 16, wherein the outer shell of the shell catalyst has a thickness of less than 300 µm.

18. The shell catalyst according to claim 17, having a Pd content of 0.5 to 2.5 wt.-%, relative to the weight of the shell catalyst.

19. The shell catalyst according to claim 18, having a Au/Pd atomic ratio of between 0 and 1.2.

20. The shell catalyst according to claim 19, wherein the outer shell contains $HfO_2$ and/or $ZrO_2$.

21. The shell catalyst according to claim 17, having an area of 90% of the shell thickness, the area being at a distance of 5% of the shell thickness from each of the outer and inner shell limits and having an average noble-metal concentration, wherein the area has a noble-metal concentration that varies from the average noble-metal concentration of this area by a maximum of +/−20%.

22. The shell catalyst according to claim 21, having a chloride content of less than 250 ppm.

23. The shell catalyst according to claim 22, further containing an alkali metal acetate.

24. The shell catalyst according to claim 23, having an alkali metal acetate content of 0.1 to 0.7 mol/l.

25. The shell catalyst according to claim 24, wherein the alkali metal/Pd atomic ratio is between 1 and 12.

26. The shell catalyst of claim 1, wherein the outer shell of the shell catalyst has a thickness in the range of 200 to 2000 µm.

27. A process for the preparation of a shell catalyst as claimed in claim 1, comprising the steps of:
   a) providing an oxidic porous catalyst support having a framework structure that contains hafnium oxide ($HfO_2$) units;
   b) depositing a solution of a Pd precursor compound onto the catalyst support;
   c) depositing a solution of an Au precursor compound onto the catalyst support the framework structure of which contains hafnium oxide units ($HfO_2$);
   d) converting the Pd component of the Pd precursor compound into the metal form; and
   e) converting the Au component of the Au precursor compound into the metal form.

28. The process according to claim 27, wherein the Pd and Au precursor compounds are selected from the group consisting of halides, oxides, nitrates, nitrites, formates, propionates, oxalates, acetates, hydroxides, hydrogen carbonates, and amine complexes or organic complexes of these metals.

29. The process according to claim 28, wherein the Pd precursor compound is selected from the group consisting of $Pd(NH_3)_4(OH)_2$, $Pd(NO_3)_2$, $K_2Pd(OAc)_2(OH)_2$, $Pd(NH_3)_2(NO_2)_2$, $K_2Pd(NO_2)_4$, $Na_2Pd(NO_2)_4$, $Pd(OAc)_2$, $PdCl_2$, $Na_2PdCl_4$, and $Pd(NH_3)_4(NO_3)_2$.

30. The process according to claim 28, wherein the Au precursor compound is selected from the group consisting of $KAuO_2$, $HAuCl_4$, $KAu(NO_2)_4$, $AuCl_3$, $NaAuCl_4$, $KAu(OAc)_3(OH)$, $HAu(NO_3)_4$ and $Au(OAc)_3$.

31. The process according to claim 27, wherein the Pd and the Au precursor compounds are deposited onto the catalyst support by steeping the catalyst support in the solution of the Pd precursor compound and in the solution of the Au precursor compound or in a solution which contains both the Pd and the Au precursor compound.

32. The process according to claim 27, wherein the solution of the Pd precursor compound and the solution of the Au precursor compound are deposited onto the catalyst support by spraying the solutions onto a fluid bed or a fluidized bed of the catalyst support, preferably by means of an aerosol of the solutions.

33. The process according to claim 27, wherein the catalyst support is heated during deposition of the solutions.

34. The process according to claim 27, wherein:
   a) a first solution of a Pd and/or an Au precursor compound is provided;
   b) a second solution of a Pd and/or an Au precursor compound is provided, wherein the first solution effects a precipitation of the metal component(s) of the precursor compound(s) of the second solution and vice versa; and
   c) the first and the second solution are deposited onto the catalyst support.

35. The process according to claim 34, wherein the precursor compound of the first solution is acid and the precursor compound of the second solution is basic.

36. The process according to claim 27, wherein the catalyst support is subjected to a fixing step once the Pd and/or the Au precursor compound has/have been deposited onto the catalyst support.

37. A process for the preparation of a shell catalyst as claimed in claim 1, comprising the steps of:
   a) providing a powdery oxidic porous catalyst support that contains hafnium oxide ($HfO_2$) units in its framework structure and wherein the catalyst support is loaded with a Pd and an Au precursor compound or with Pd and Au particles;
   b) depositing the loaded catalyst support onto a shaped body in the form of a shell;
   c) calcining the loaded shaped body according to step b); and
   d) optionally, converting the Pd and the Au component of the Pd or Au precursor compound into the metal form.

* * * * *

UNITED STATES PATENT AND TRADEMARK OFFICE
CERTIFICATE OF CORRECTION

PATENT NO. : 8,466,082 B2
APPLICATION NO. : 12/601399
DATED : June 18, 2013
INVENTOR(S) : Hagemeyer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 536 days.

Signed and Sealed this
Eighth Day of September, 2015

Michelle K. Lee
*Director of the United States Patent and Trademark Office*